United States Patent [19]  
Tiley et al.

[11] Patent Number: 4,933,474  
[45] Date of Patent: Jun. 12, 1990

[54] PROCESS FOR THE PREPARATION OF MACROLIDE COMPOUNDS

[75] Inventors: Edward P. Tiley, Pinner; Michael V. J. Ramsay, South Harrow, both of United Kingdom

[73] Assignee: American Cyanamid Company, Stamford, Conn.

[21] Appl. No.: 242,221

[22] Filed: Sep. 9, 1988

[30] Foreign Application Priority Data

Sep. 11, 1987 [GB] United Kingdom ................. 8721375

[51] Int. Cl.$^5$ .......................................... C07D 315/00
[52] U.S. Cl. ................................................. 549/264
[58] Field of Search .......................................... 549/264

[56] References Cited

U.S. PATENT DOCUMENTS 4,579,864 4/1986 Linn et al. ............................ 549/264
4,581,345 4/1986 Wyuratt, Jr. ......................... 549/264

FOREIGN PATENT DOCUMENTS 238258 9/1987 European Pat. Off. .
2166436A 5/1986 United Kingdom .
2176182 12/1986 United Kingdom ................. 549/264

Primary Examiner—Glennon H. Hollrah  
Assistant Examiner—Amelia A. Owens  
Attorney, Agent, or Firm—Bacon & Thomas

[57] ABSTRACT

A process is described for preparing a compound of formula (I)

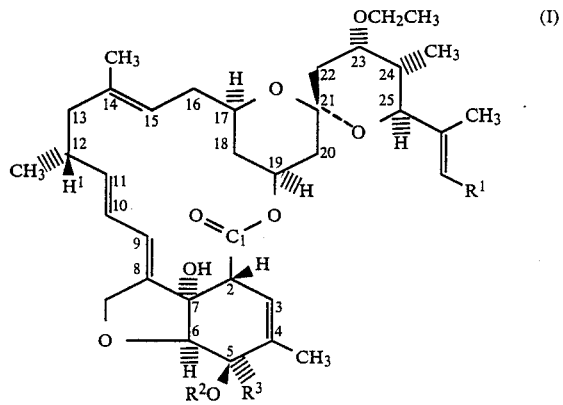

(in which $R^1$ represents a methyl, ethyl or isopropyl group, $R^2$ represents a hydrogen atom or a methyl or acetyl group and $R^3$ represents a hydrogen atom, or $OR^2$ and $R^3$ together with the carbon atom to which they are attached represent the group $>C=O$) which comprises treating a corresponding 23α- compound with a triethyloxonium salt.

3 Claims, No Drawings

PROCESS FOR THE PREPARATION OF MACROLIDE COMPOUNDS

This invention relates to a novel process for the preparation of macrolide compounds.

The compounds of formula (I)

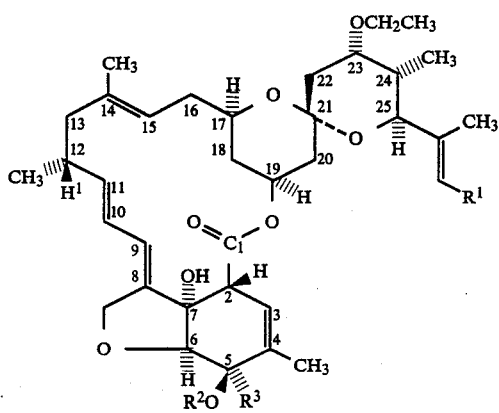

in which $R^1$ represents methyl, ethyl or isopropyl group, $R^2$ represents a hydrogen atom or a methyl or acetyl group and $R^3$ represents a hydrogen atom are described in UK Patent Specification 2176182A, and the corresponding 5-keto compounds in which $OR^2$ and $R^3$ together with the carbon atom to which they are attached represent the group $>C=O$ are described in European Patent Specification 0238258A.

These compounds have anti-endoparasitic, anti-ectoparasitic, anti-fungal, insecticidal, nematicidal and acaricidal activity and are useful in combating parasites in animals and humans and pests in agriculture, horticulture, forestry, public health and stored products. The compounds may also be used as intermediates in the preparation of other active compounds.

The present invention provides a novel and useful synthesis of the compounds of formula (I) from fermented starting materials. The process is convenient to use and provides the compounds of formula (I) in good yield.

Thus, we provide a process for preparing a compound of formula (I) which comprises treating a compound of formula (II)

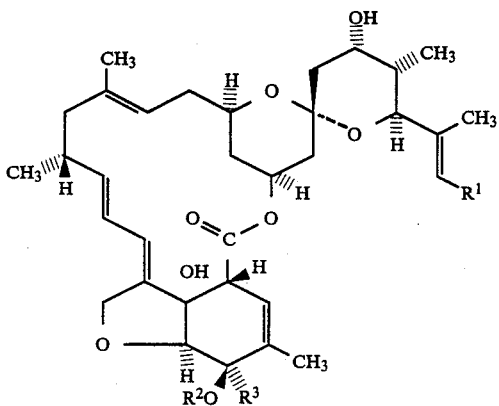

(wherein $R^1$, $R^2$ and $R^3$ are as defined previously) with a triethyloxonium salt (eg triethyloxonium tetrafluoroborate), followed by deacetylating a compound of formula (I) in which $OR^2$ is an acetyloxy group when a compound of formula (I) in which $OR^2$ is a hydroxy group is required.

The reaction may be carried out in a solvent such as a halogenated hydrocarbon e.g. methylene chloride, and preferably in the presence of a base such as an alkali metal carbonate (e.g. sodium carbonate or potassium carbonate) or an alkaline earth metal carbonate (e.g. calcium carbonate). The reaction temperature is conveniently 10°–40° C.

Deacetylation to provide a compound of formula (I) in which $OR^2$ is a hydroxy group may be performed using base hydrolysis e.g. using sodium or potassium hydroxide in aqueous alcohol or by acid hydrolysis e.g. using concentrated sulphuric acid in methanol.

The compounds of formula (II) in which $R^1$ is as defined previously and $OR^2$ represents a hydroxy or methoxy group may be obtained using the fermentation and isolation methods described in UK Patent Specification No. 2166436A. Compounds of formula (II) in which $OR^2$ represents an acetyloxy group may be prepared from the corresponding 5-OH compounds using standard acetylation procedures.

Thus, for example, acetylation may be effected using an acetylating agent such as acetic acid or a reactive derivative thereof, such as an acetyl halide (e.g. acetyl chloride), anhydride or activated ester, or a reactive derivative of a carbonic acid $CH_3OCOOH$ or thiocarbonic acid $CH_3OCSOH$.

Acetylations employing acetyl halides and anhydrides may if desired be effected in the presence of an acid binding agent such as a tertiary amine (e.g. triethylamine, dimethylaniline or pyridine), inorganic bases (e.g. calcium carbonate or sodium bicarbonate), and oxiranes such as lower 1,2-alkylene oxides (e.g. ethylene oxide or propylene oxide) which bind hydrogen halide liberated in the acetylation reaction.

Acetylation employing acetic acid is desirably conducted in the presence of a condensing agent, for example a carbodiimide such as N,N'-dicyclohexylcarbodiimide or N-ethyl-N'γ-dimethylaminopropylcarbodiimide; a carbonyl compound such as carbonyldiimidazole; or an isoxazolium salt such as N-ethyl-5-phenylisoxazolium perchlorate.

An activated ester may conveniently be formed in situ using, for example, 1-hydroxybenzotriazole in the presence of a condensing agent as set out above. Alternatively, the activated ester may be performed.

The acetylation reaction may be effected in aqueous or non-aqueous reaction media, conveniently at a temperature in the range $-20°$ to $+100°$ C., e.g. $-10°$ to $+50°$ C.

The compounds of formula (II) in which $OR^2$ and $R^3$ together with the carbon atom to which they are attached represent $>C=O$ (hereinafter referred to as '5-keto compounds of formula (II)') may be prepared by cultivating Streptomyces thermoarchaensis NCIB 12015 or a mutant thereof and isolating the compound from the fermentation broth so obtained.

The Streptomyces organism may be cultured by conventional means, i.e. in the presence of assimilable sources of carbon, nitrogen and mineral salts. Assimilable sources of carbon, nitrogen and minerals may be provided by either simple or complex nutrients for example as described in UK Patent Specification 2166436A.

Cultivation of the Streptomyces organism will generally be effected at a temperature of from 20° to 50° C. preferably from 25° to 40° C., and will desirably take place with aeration and agitation e.g. by shaking or stirring. The medium may initially be inoculated with a small quantity of a sporulated suspension of the microorganism but in order to avoid a growth lag a vegetative inoculum of the organism may be prepared by inoculating a small quantity of the culture medium with the spore form of the organism, and the vegetative inoculum obtained may be transferred to the fermentation medium, or, more preferably to one or more seed stages where further growth takes place before transfer to the principal fermentation medium. The fermentation will generally be carried out in the pH range 5.5 to 8.5.

The fermentation may be carried out for a period of 2-10 days, e.g. about 5 days.

The 5-keto compounds of formula (II) may be separated from the whole fermentation broth so obtained by conventional isolation and separation techniques. A variety of fractionation techniques may be used, for example adsorption-elution, precipitation, fractional crystallisation, solvent extraction and liquid-liquid partition which may be combined in various ways. Solvent extraction, partition between two solvents which are immiscible or only partially miscible with each other and chromatography have been found to be most suitable for isolating and separating the compound.

The invention is illustrated but not limited by the following Example in which temperatures are in °C., 'L' represents liter and EtOH represents ethanol. Compounds are named as derivatives of 'Factor A', which is the compound of formula (II) in which $R^1$ represents isopropyl and $OR^2$ is a hydroxy group. The preparation of 5-keto Factor A is described in British Patent Specification 2187742A. EXAMPLE 1

23-Ethoxy 5-keto Factor A

A solution of 5-keto Factor A (611 mg) in dry dichloromethane (10 ml) was stirred at 20° under nitrogen, and calcium carbonate (600 mg) and triethyloxonium tetrafluoroborate (5 ml of 1M-solution in dichloromethane) were added. The resulting suspension was stirred for 3 days under nitrogen, then diluted with ethyl acetate (100 ml), washed with 2N-hydrochloric aced (100 ml), water (50 ml), and brine (50 ml), and dried (magnesium sulphate), and evaporated to dryness. The residue (670 mg) was purified by chromatography over Kieselgel 60 (80 g); the column was eluted with light petroleum:ethyl acetate (4:1). Combination of the appropriate fractions gave a foam (126 mg), which crystallised from light petroleum (ca 3 ml) to provide the *title compound* (75 mg) as a colourless solid, m.p. 133° to 135°, $[\alpha]_D^{21} + 127°$ (c 0,39, $CHCl_3$), $\lambda_{max}$ (EtOH) 240 nm ($\epsilon$ 29,200), $\nu_{max}$ ($CHBr_3$) 3500 (OH), 1708 (ester) and 1676 cm$^{-1}$ (enone), $\delta$ ($CDCl_3$) include 6.57 (broad s, 1H), 3.64 (m, 1H), 3.46 (m, 1H), 3.26 (m, 1H), 1.14 (t, J7 Hz, 3H) and 0.74 (d, J 6 Hz, 3H).

We claim:

1. A process for preparing a compound of formula (I)

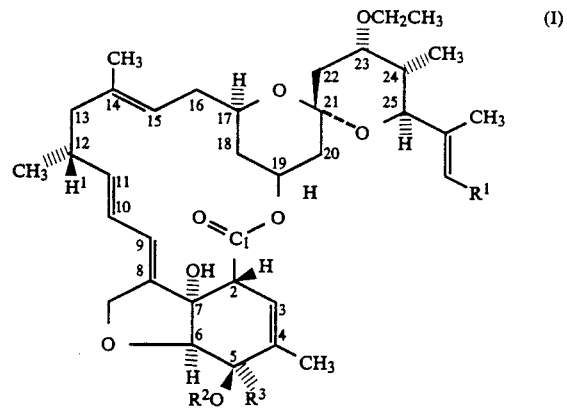

(in which $R^1$ represents a methyl, ethyl or isopropyl group, $R^2$ represents a hydrogen atom or a methyl or acetyl group and $R^3$ represents a hydrogen atom, or $OR^2$ and $R^3$ together with the carbon atom to which they are attached represent the group $>C=O$) which comprises treating a compound of formula (II)

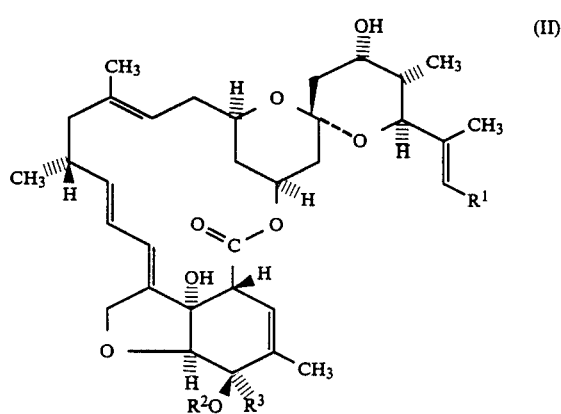

(wherein $R^1$, $R^2$ and $R^3$ are as defined previously) with a triethyloxonium salt, followed by deacetylating a compound of formula (I) in which $OR^2$ is an acetyloxy group when a compound of formula (I) in which $OR^2$ is a hydroxy group is required.

2. A process according to claim 1 in which said salt is triethyloxonium tetrafluoroborate.

3. A process according to claim 1 in which the reaction is carried out in the presence of sodium carbonate, potassium carbonate or calcium carbonate.

* * * * *

UNITED STATES PATENT OFFICE
CERTIFICATE OF CORRECTION Page 1 of 2

Patent No. 4,933,474    Dated June 12, 1990

Inventor(s) Edward P. Tiley et al.

It is certified that error appears in the above-identified patent and that said Letters Patent is hereby corrected as shown below:

Col. 4, lines 5 to 23, position 19 reading "  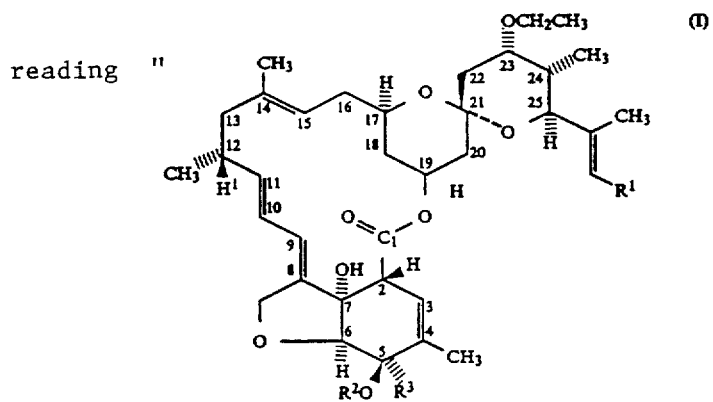  "

UNITED STATES PATENT AND TRADEMARK OFFICE
CERTIFICATE OF CORRECTION

PATENT NO. : 4,933,474

DATED : June 12, 1990

INVENTOR(S) : Edward P. Tiley et al

It is certified that error appears in the above-identified patent and that said Letters Patent is hereby corrected as shown below:

should read

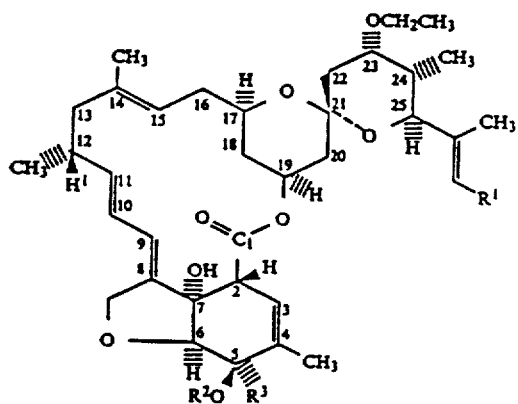

Signed and Sealed this

Twenty-ninth Day of October, 1991

Attest:

HARRY F. MANBECK, JR.

*Attesting Officer*    *Commissioner of Patents and Trademarks*